United States Patent
Li et al.

(10) Patent No.: US 11,543,545 B2
(45) Date of Patent: Jan. 3, 2023

(54) METHOD AND APPARATUS TO USE A BROAD-SPECTRUM ENERGY SOURCE TO CORRECT A NONLINEAR ENERGY RESPONSE OF A GAMMA-RAY DETECTOR

(71) Applicant: CANON MEDICAL SYSTEMS CORPORATION, Otawara (JP)

(72) Inventors: Xiaoli Li, Vernon Hills, IL (US); Yi Qiang, Vernon Hills, IL (US); Kent C. Burr, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/788,741

(22) Filed: Feb. 12, 2020

(65) Prior Publication Data

US 2021/0247530 A1    Aug. 12, 2021

(51) Int. Cl.
*A61B 6/03* (2006.01)
*G01T 1/202* (2006.01)
*G01T 7/00* (2006.01)
*G01T 1/24* (2006.01)
*G01T 1/29* (2006.01)
(Continued)

(52) U.S. Cl.
CPC .............. *G01T 7/005* (2013.01); *A61B 6/037* (2013.01); *A61B 6/585* (2013.01); *G01T 1/202* (2013.01); *G01T 1/2018* (2013.01); *G01T 1/248* (2013.01); *G01T 1/249* (2013.01); *G01T 1/2985* (2013.01); *A61B 6/4258* (2013.01)

(58) Field of Classification Search
None
See application file for complete search history.

(56) References Cited

U.S. PATENT DOCUMENTS 6,835,935 B2 * 12/2004 Engdahl ................ G01T 1/1642
250/252.1
7,129,495 B2 * 10/2006 Williams ................ G01T 1/172
250/363.03
(Continued)

FOREIGN PATENT DOCUMENTS

EP            3745161 A1 * 12/2020 ............... G01T 1/36
JP        2020197523 A  * 12/2020 ............. G01T 7/005

*Primary Examiner* — Thomas R Artman
(74) *Attorney, Agent, or Firm* — Oblon, McClelland, Maier & Neustadt, L.L.P.

(57) ABSTRACT

A method and apparatus are provided for nonlinear energy correction of a gamma-ray detector using a calibration spectrum acquired from the background radiation of lutetium isotope 176 (Lu-176) present in scintillators in the gamma-ray detector. Further, by periodically acquiring Lu-176 spectra using the background radiation from the scintillators, the nonlinear energy correction can be monitored to detect when changes in the gamma-ray detector cause the detector to go out of calibration, and then use a newly acquired Lu-176 spectrum to update the calibration of the nonlinear energy correction as needed. The detector calibration is performed by comparing a reference histogram to a calibration histogram generated using the nonlinear energy correction, and adjusting the parameters of the nonlinear energy correction until the two histograms match. Alternatively, the detector calibration is performed by comparing reference and calibration values for specific spectral features, rather than for the whole Lu-176 spectrum.

27 Claims, 12 Drawing Sheets

(51) Int. Cl.
*G01T 1/20* (2006.01)
*A61B 6/00* (2006.01)

(56) References Cited

U.S. PATENT DOCUMENTS

| | | | |
|---|---|---|---|
| 7,633,057 B2 | 12/2009 | Cooke et al. | |
| 8,119,980 B2* | 2/2012 | Malmin | G01T 1/40 |
| | | | 250/252.1 |
| 9,360,570 B2 | 6/2016 | Rothfuss et al. | |
| 10,126,444 B2* | 11/2018 | Zhao | G01T 1/208 |
| 10,436,915 B2* | 10/2019 | Teshigawara | G01T 1/40 |
| 10,527,741 B2* | 1/2020 | Cho | G01T 7/005 |
| 10,732,300 B2* | 8/2020 | Laurence | G01T 7/005 |
| 10,775,520 B2* | 9/2020 | Cho | G01T 7/005 |
| 11,255,985 B2* | 2/2022 | Burr | G01T 1/36 |
| 2006/0102845 A1* | 5/2006 | Williams | G01T 1/2985 |
| | | | 250/363.03 |
| 2008/0251709 A1* | 10/2008 | Cooke | G01T 1/2985 |
| | | | 250/252.1 |
| 2015/0301201 A1* | 10/2015 | Rothfuss | G01T 1/40 |
| | | | 250/252.1 |
| 2016/0299240 A1* | 10/2016 | Cho | G01T 7/005 |
| 2017/0090051 A1* | 3/2017 | Zhao | G01T 1/20 |
| 2018/0341027 A1* | 11/2018 | Laurence | G01T 1/2985 |
| 2019/0086557 A1* | 3/2019 | Teshigawara | G01T 1/40 |
| 2020/0072988 A1* | 3/2020 | Cho | G01T 7/005 |
| 2020/0379133 A1* | 12/2020 | Burr | G01T 7/005 |
| 2021/0247530 A1* | 8/2021 | Li | A61B 6/585 |

* cited by examiner

METHOD AND APPARATUS TO USE A BROAD-SPECTRUM ENERGY SOURCE TO CORRECT A NONLINEAR ENERGY RESPONSE OF A GAMMA-RAY DETECTOR

FIELD

This disclosure relates to energy detection in a gamma-ray detector, and, more particularly, to calibrating energy corrections of the gamma-ray detector using a single (or at most a few) energy source having more spectral features than just a single energy peak.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

In positron emission tomography (PET) imaging, a tracer agent is introduced into the patient, and the physical and bio-molecular properties of the agent cause it to concentrate at specific locations in the patient's body. The tracer emits positrons, resulting in annihilation events occurring when the positron collides with an electron to produce two gamma rays (at 511 keV) traveling at substantially 180 degrees apart.

PET imaging systems use detectors positioned around the patient to detect coincidence pairs of gamma rays. A ring of detectors can be used in order to detect gamma rays coming from each angle. Thus, a PET scanner can be substantially cylindrical to be maximize the capture of the isotropic radiation. A PET scanner can be composed of several thousand individual crystals (e.g., Lutetium Orthosilicate (LYSO) or other scintillating crystal) which are arranged in two-dimensional scintillator arrays that are packaged in modules with photodetectors to measure the light pulses from respective scintillation events. For example, the light from respective elements of a scintillator crystal array can be shared among multiple photomultiplier tubes (PMTs) or can be detected by silicon photomultipliers (SiPMs) having a one-to-one correspondence with the elements of a scintillator crystal array.

To reconstruct the spatio-temporal distribution of the tracer via tomographic reconstruction principles, each detected event is characterized for its energy (i.e., amount of light generated), its location, and its timing. By detecting the two gamma rays, and drawing a line between their locations, i.e., the line-of-response (LOR), one can determine the likely location of the original disintegration. The timing information can also be used to determine a statistical distribution for the annihilation along the LOR based on time-of-flight (TOF) information of the two gamma rays. By accumulating a large number of LORs, tomographic reconstruction can be performed to determine a volumetric image of the spatial distribution of radioactivity (e.g., tracer density) within the patient.

Single-photon emission computed tomography (SPECT) is similar to PET except a collimator is used to restrict the solid angle of gamma rays incident on the respective detector elements (e.g., the respective elements in the scintillator crystal array), making reconstruction possible using single gamma-ray detection events as opposed to requiring coincidences to determine a LOR.

In addition to position information (e.g., the LOR) and timing information (e.g., the TOF), detectors in PET and SPECT systems can also acquire and use energy information in the image reconstruction process. Energy calibration is important for all PET detectors. For example, proper energy calibration allows energy cuts to be made to greatly reduce the contribution of scatter to the final image.

In many PET detectors, the energy response of the detector is nearly linear. In these cases, energy calibration can be done using a single energy. In the case of linear response, the energy calibration consists of determining a scale factor that translates the measured signal level corresponding to 511 keV gamma rays to a desired target value.

However, energy measurements can deviate from an ideal linear response due to nonlinearities in the measurement process and/or practical considerations related to, e.g., light/charge sharing among channels during a multi-channel gamma-ray detection (e.g., due to the gamma-ray energy being absorbed in multiple detectors/channels as can happen due to Compton scattering). Accordingly, improved techniques are desired to correct energy measurements in pixelated gamma-ray detectors.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1A:
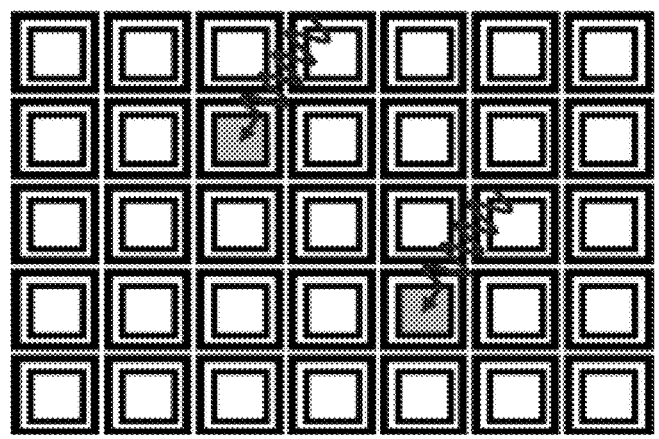
FIG. 1A shows a diagram a silicon photomultiplier (SiPM) detector with two optical photons incident on respective microcells, according to one implementation.

Certain implementations of both positron emission tomography (PET) and single-photon emission computed tomography (SPECT) imaging can depend on the ability to determine the position, time, and energy of detected gamma rays. For example, time and energy windowing can be used to distinguish scattered and random gamma rays from coincident gamma rays originating from the same positron annihilation event. Thus, the reliability of the coincidence discrimination can depend on the accuracy of the timing and energy calibrations.

Accordingly, improved energy calibrations for gamma-ray detectors are desired. However, these improved method should avoid, as much as possible, increasing the time and expense of the energy calibrations. For example, the improved method should, if possible, reduce the number of energy calibration sources and the number of steps in the calibration procedure. That is, the improved calibration method should strive to both provide more accurate energy calibrations while also being more efficient with respect to time and cost.

The detector response as a function of the input energy can deviate from an ideal linear response due to various practical considerations. To correct for this nonlinear energy response, the methods and apparatuses described herein use improved energy calibration method to generate corrected energy values that are substantially linear.

There can be many sources of nonlinearity in the gamma-ray detection process. For example, the use of silicon photomultipliers (SiPMs) as the photosensor in scintillator-based gamma-ray detectors and the time-over-threshold (ToT) method for amplitude estimation can both result in significant energy nonlinearity. Correcting this nonlinearity is important for achieving accurate energy information, especially for multi-channel detection events in which the energy gamma rays becomes distributed and detected among multiple crystals (e.g., the energy can be shared among multiple crystals due to Compton scattering). Additional details regarding the effects of energy nonlinearity on the detection of multi-channel events are provided later in reference to FIG. 3.

Energy signals can be acquired by the energy deposited in a crystal being converted to an electrical signal, and the electrical signal can then be digitized. This digitization process can be performed by various methods. Among the methods for digitizing the energy measurements of gamma rays, the time-over-threshold (TOT) method has the advantages of being cost effective and can be easily applied to applications requiring high channel density. Although the TOT value is a monotonically increasing function of the absorbed energy in a given channel, the relation between the TOT and the actual energy can deviate from being perfectly linear. This nonlinear detector response as well as other nonlinear detector responses can be corrected using the methods described herein.

When a detector's sensitivity element is a crystal array, inter crystal scattering (e.g., Compton scattering), light sharing, and charge sharing can result in the energy of the incident gamma ray being shared between multiple crystals/readout channels. That is, the energy from a single 511 keV gamma ray is shared/distributed across multiple channel, such that each of these channels detects only a fraction of the total energy of the gamma ray. However, the total energy of the original gamma ray can be recovered by summing the energies from the respective channels, but only if the non-linearities are corrected for.

Because, in a multi-channel detection event, the energy detected by a given channel can range from 511 keV to a lower detection limit of the gamma-ray detector (e.g., 80 keV), the energy calibration of the gamma-ray detector will preferably span this range.

One method of calibrating over a broad range of energies is to use multiple sources (e.g., different isotopes) emitting different energies. For example, external gamma-ray sources or radiation background from the crystal can be used to provide gamma rays with different energies.

In contrast to multi-source calibration methods, the methods described herein use a gamma-ray source with a highly structured energy signature that by itself spans many different gamma-ray energies (e.g., many discrete energies and/or a continuum of energies). Accordingly, the energy calibration of a broad range of gamma-ray energies can be performed using a single gamma-ray source (e.g., lutetium isotope 176, Lu-176) or in some implementations two gamma-ray sources (e.g., the second radiation source can be germanium isotope, Ge-68, or fluorine isotope 18, F-18).

For example, gamma-ray detectors using silicon photomultipliers and time-over-threshold amplitude estimation exhibit significant energy nonlinearity. In certain implementations, the methods described herein extract nonlinearity correction factors using two or more spectral features of a Lu-176 background spectrum. Lutetium (Lu)-based scintillators are often used for time-of-flight (TOF) measurements in positron emission tomography (PET) detectors. Because Lu-176 is weakly radioactive, a background spectrum can be accumulated over time whenever the PET scanner is not being used. This background spectrum does not require any outside radiation sources because the built into the PET scanner as part of the scintillators used for detection. Thus, the additional effort to acquire the energy calibration spectrum can be minimized Referring now to the drawings, wherein like reference numerals designate identical or corresponding parts throughout the several views, FIGS. 1A-1C illustrate a first source of nonlinearity, which arises in silicon photomultiplier (SiPM), and FIGS. 2A and 2B illustrate a second source of nonlinearity, which arises when time-over-threshold (TOT) values is used as a measure of gamma-ray energy.

Figure 1B:
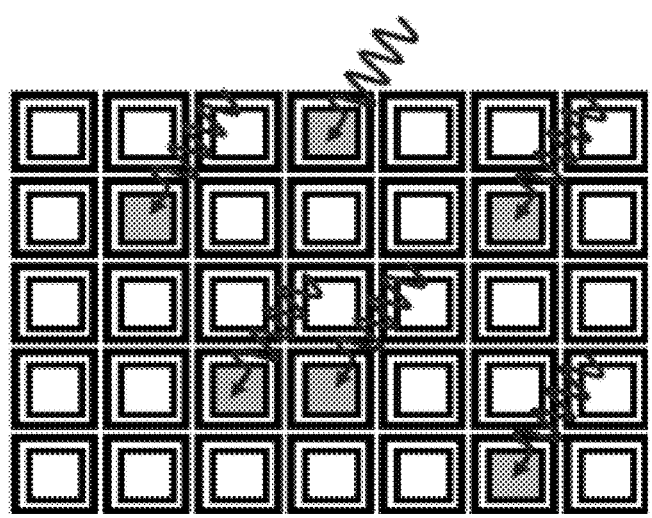
FIG. 1B shows a diagram the SiPM detector with six optical photons incident on the respective microcells, according to one implementation.
Figure 1C:
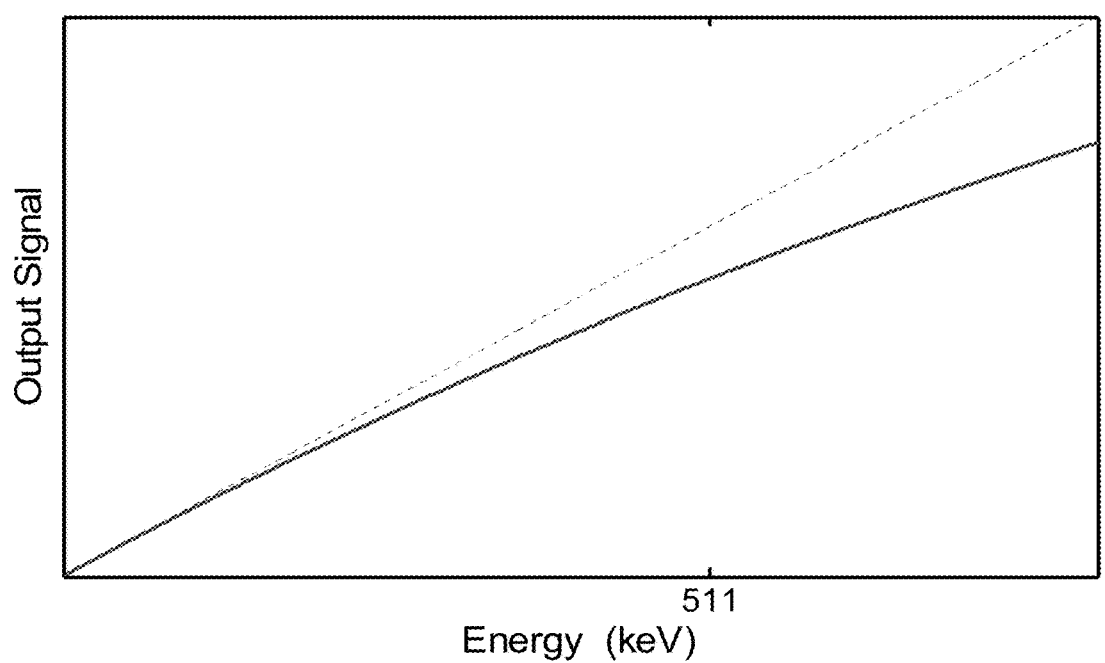
FIG. 1C shows a nonlinear energy response of the SiPM detector, according to one implementation.

FIG. 1A shows a SiPM detector in a low-flux case in which two photons are incident on two micro-cells within the two-dimensional (2-D) array of 35 micro-cells (i.e., five micro-cells by seven micro-cells). Often, a SiPM detector will have several thousand micro-cells, but here a reduced number of micro-cells is used as a simplified example for illustrative purposes. FIG. 1B shows the SiPM detector in a medium-flux case in which six photons are incident on six of the 35 micro-cells. The SiPM is a photodetector formed as a 2-D array of tiny Geiger-mode avalanche photodiodes (G-APD) elements, which are referred to as microcells. This architecture overcomes the disadvantage of a single G-APD because the amplitude of the output pulse of a SiPM is proportional (over some range of intensities) to the number of photons incident on the surface of the device. However, when the photon flux becomes high enough that the probability two photons being incident at the same micro-cell is no longer negligible, then the signal as a function of the number of incident photons begins to roll over, becoming nonlinear. This nonlinearity is illustrated in FIG. 1C in which the gamma-ray energy, which is represented along the horizontal axis, is proportional to the number of optical photons incident on the SiPM. In PET detectors, the optical photon flux can be high (e.g., thousands of optical photons generated per 511 keV gamma ray), necessitating a large dynamic range for the SiPMs.

As previously discussed, the output signal of a SiPM is the sum of the signals of the firing micro-cells, and the output signal is therefore correlated to the number of incident photons. The dynamic range is determined by the number of cells in the device, and linearity of the SiPM signal with light intensity is only maintained as long as no more than one optical photon interacts per SiPM cell. At higher light intensities where this condition is violated, there will be saturation of the signal leading to nonlinearity with the incident light levels. In the case of PET, this will result in a nonlinearity between the detector signal and the energy deposited in the scintillator, thus degrading the ability to reject Compton-scattered annihilation photons based on their energy loss, or to reject pulse pile-up due to two annihilation photons interacting in the same scintillator element at the same time.

Figure 2A:
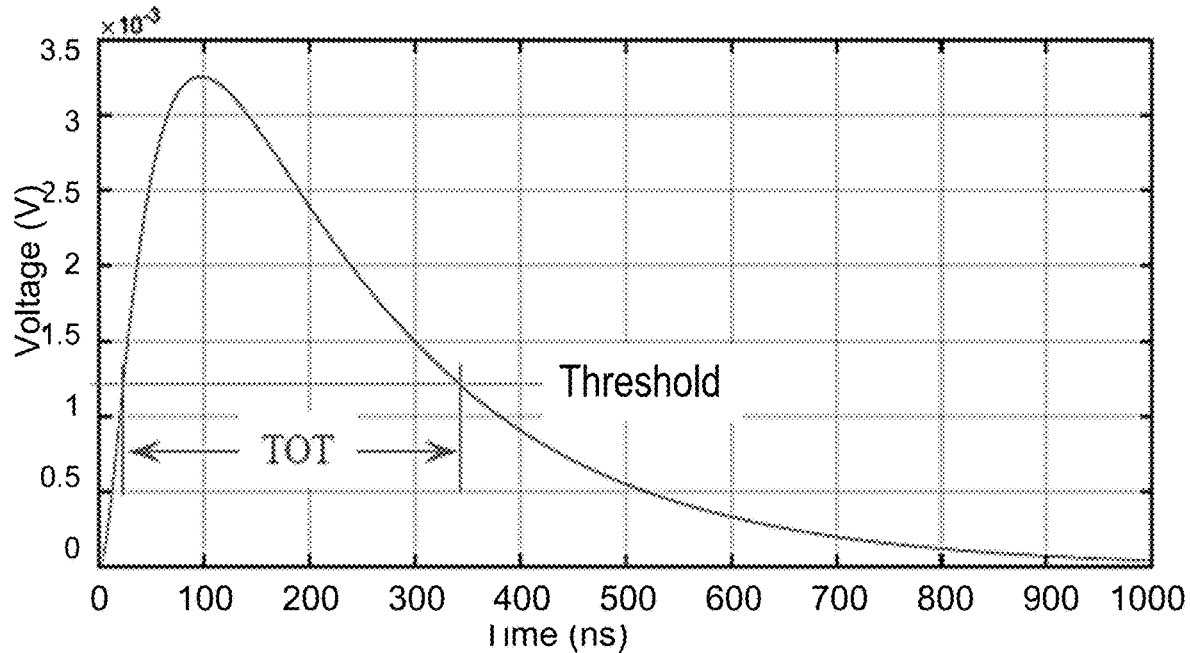
FIG. 2A shows a plot of a time-over-threshold (TOT) measurement, according to one implementation.
Figure 2B:
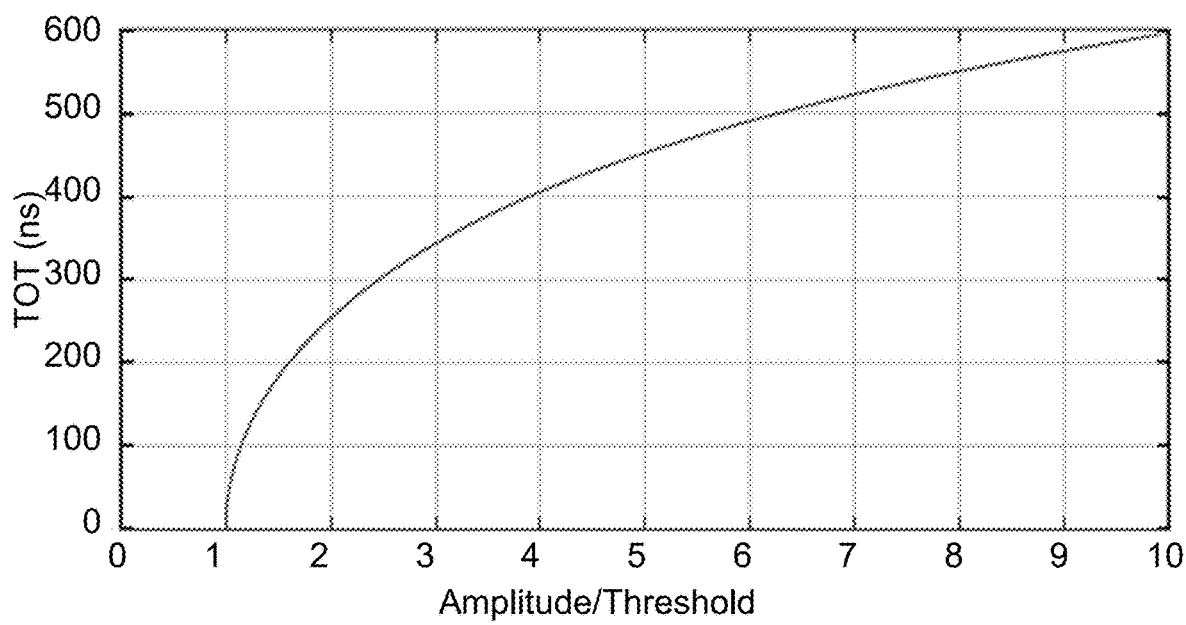
FIG. 2B shows a plot of the TOT as a function of the ratio peak height to the threshold, according to one implementation.

FIG. 2A shows a plot of a pulse from the detection of a gamma ray with the voltage plotted along the vertical axis and time plotted along the horizontal axis. Further, FIG. 2A shows a predefined threshold at about 1.2 millivolts, and the duration of time that the pulse exceeds this threshold is the TOT value. As illustrated in FIG. 2B, the TOT value is monotonically related to the energy of the detected gamma ray, which can be represented by the area under the curve of the pulse, or by the amplitude of the pulse. For signals below the threshold no signal/detection is registered.

In addition to the above-illustrated detector-saturation nonlinearity and the TOT nonlinearity, PET detectors can suffer from additional sources of nonlinearity. Regardless of the source or type of nonlinearity, the calibration methods described herein is general, and can be applied to any and all detector nonlinearities regardless of the source of the nonlinearities. That is, although detector saturation and TOT nonlinearities are used for illustrative purposes herein, these examples of PET detection nonlinearities are not limiting.

The errors introduced by nonlinearities can be compounded by multi-channel detection events, which occur when the energy from a single gamma ray is shared and then detected among multiple detector elements (e.g., by Compton scattering, optical cross-talk, etc.). Although the total energy can be recovered by determining which detection events are multi-channel events, and then identify groups of multi-channel events arising from the same gamma ray (e.g., based on the coincidence of their detection times, spatial proximity, and/or respective energies). Then the measured energies from all of the events arising from the same gamma ray can be summed to aggregate the shared energies and reassemble the total energy of original gamma ray. That is, respective energies from the detector amongst which the energy was shared are summed to determine the total energy of the gamma ray. Without correcting for the nonlinearities, summing the raw energy signals will result in a total energy value that differs (e.g., is greater than) would be registered if the energy were measured as a single-channel detection event, as shown in FIG. 3.

Figure 3:
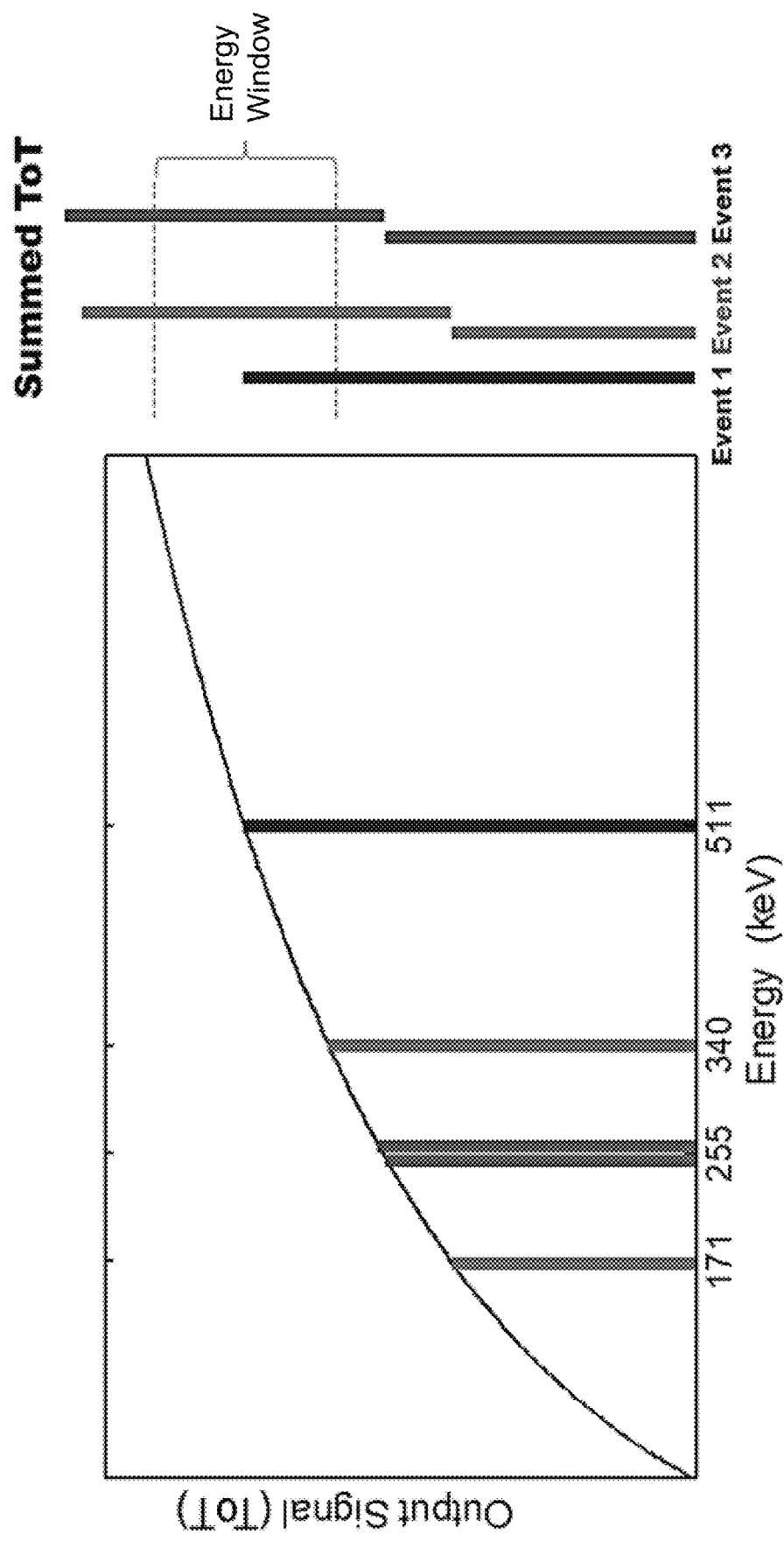
FIG. 3 shows how the raw measured energies for one-channel detection events differ from the sum of the raw measured energies of two-channel detection events, according to one implementation.

In particular, FIG. 3 illustrates the case of the nonlinearity arising from TOT measurements, contrasting single-channel events with multi-channel detection events. Event 1 is a single-channel detection event in which the entire gamma-ray energy of 511 keV is deposited in a single crystal. To the right is shown an energy window, which is centered on the 511 keV energy of gamma rays from positron-electron annihilation. Events 2 and 3 correspond to two-channel detection events in which two crystals each detect a portion of the total 511 keV energy of the gamma ray.

In event 2, 171 keV is detected by a first crystal, and 340 keV is detected by a second crystal (i.e., the total energy is 171 keV+340 keV=511 keV). In event #3, the first and second crystals absorb/detect energies of 255 keV and 256 keV, respectively. As shown on the right-hand-side of FIG. 3, without a nonlinearity correction, the sum of the energies for each of events #2 and #3 fall outside the designated energy window. Although both events deposit a total of 511 keV, the absence of a nonlinearity correction to the measured signals results in their summed-signals being much greater than would be registered for single-channel detection of 511 keV, and therefore the events would be discarded, resulting in reduced sensitivity.

For example, it is not uncommon for 65% of the detection events in the a scintillator and SiPM-based gamma-ray detector to be single crystal/single channel detection events, with Compton scattering causing 30% of detected gamma rays to be two-channel detection events and 5% to be three-channel detection events. In this case, excluding the multi-channel detection events reduces the singles count rate to 65% efficiency, and reduces the coincidence count rate to 42% efficiency. Because PET imaging relies on coincidence detection to determine the line of response (LOR), excluding the multi-channel detection events reduces the overall sensitivity by more than 50%.

As used herein, the term "energy" is not restricted to mean a calibrated energy that is linearly related to the actual or true energy. In general, the term "energy", as used herein, specifies an energy coordinate that represents and is related monotonically to the actual or true energy. Thus, the term "energy" does not necessarily refer to actual or true energy, unless context clearly indicates otherwise.

For example, when the summing of energies is discussed herein, this summing can be performed on "energy coordinates," rather than a calibrated value that is linearly related to the actual energy. The relation of the measured/raw energy $E_{raw}$ (i.e., "energy coordinates") can be related to the true energy $E_{true}$ by a nonlinear function $E_{true}=f(E_{raw})$ and the inverse function can be applied to map from the true energy to the measured, raw energy value according to $E_{raw}=f^{-1}(E_{true})$. Because the relation between measured, raw energy to the true energy is nonlinear, the sum of two measured energies $f^{-1}(E_1)$ and $f^{-1}(E_2)$ from two-channel detection does not equal the measured/raw energy for an equivalent single-channel detection, i.e., $f^{-1}(E_1)+f^{-1}(E_2) \neq f^{-1}(E_1+E_2)$, wherein $E_1+E_2=E_{Total}$, and $E_{Total}$ is the true energy of the incident, e.g., 511 keV. Accordingly, to accurately compare the energies of multi-channel detections with signal-channel detections, an energy calibration and correction is applied individually to each of the energies before summing the energies of the multi-channel detections.

As discussed above, the methods described herein can be better understood by contrasting them with related calibration methods that use many discrete sources and isotopes for energy calibration. For example, these related methods for calibrating the nonlinearity involve making measurements with multiple isotopes to derive the spectral positions of multiple energies covering the range of intended use. In a production or clinical setting, the use of this method is undesirable because frequently replacing multiple isotopes is expensive and the measurements are time consuming and tedious.

However, a multi-source energy calibration might still be useful in the initial (primary) calibration of a PET scanner (e.g., when the PET scanner is initially installed). Then subsequent (secondary) calibrations can be performed using an abbreviated calibration process performed to update the energy correction using just the Lu-176 spectrum or the Lu-176 spectrum in combination with a spectrum from another radioactive isotope. Because the initial/primary calibration is a onetime event (or at least an infrequent event) the extra burden of a more involved calibration procedure can be justified, whereas recalibrations/updating the energy calibration can occur more frequently, and therefore minimizing the time and effort required for recalibrations is of greater importance.

Figure 4:
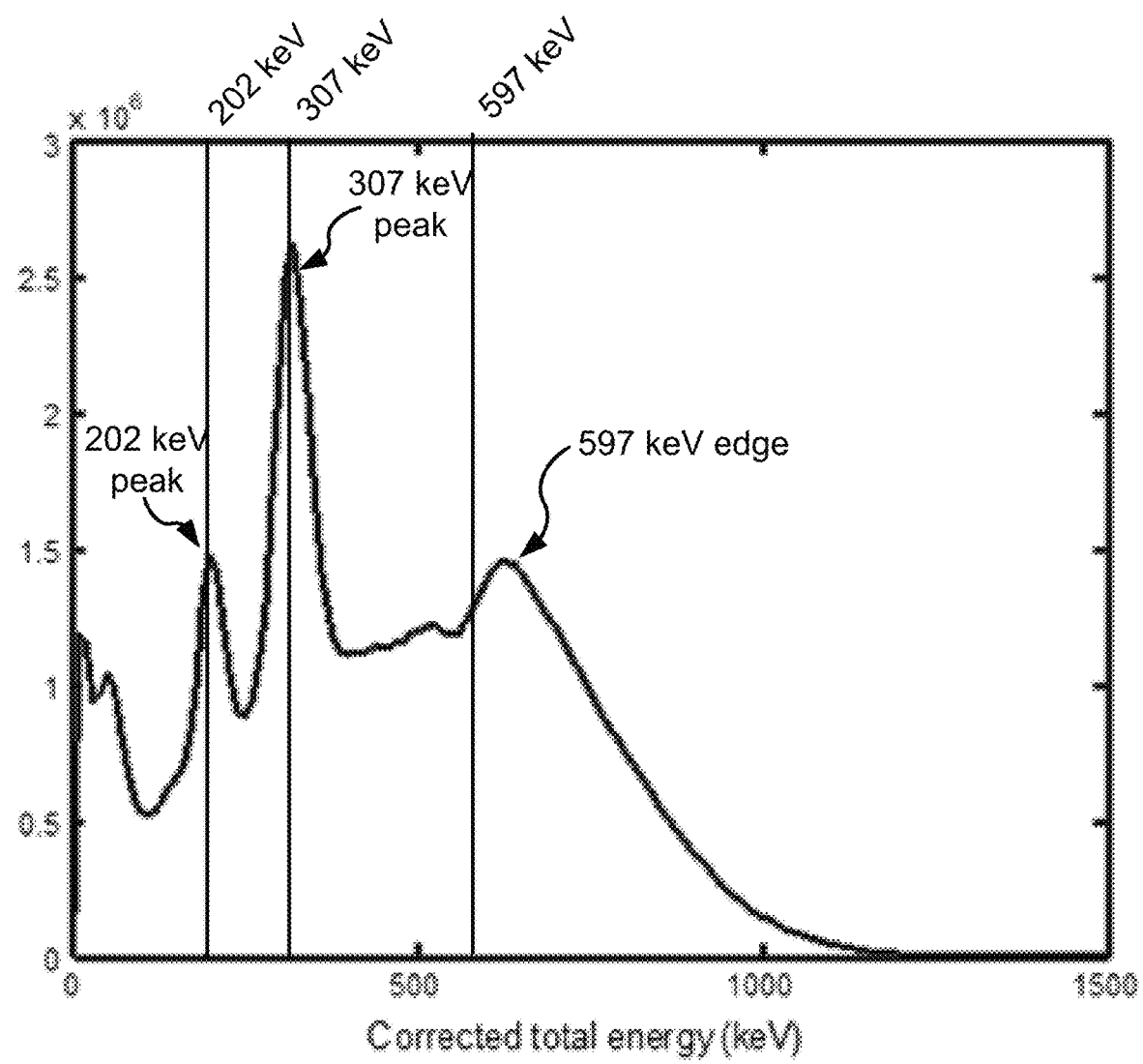
FIG. 4 shows a lutetium isotope 176 (Lu-176) spectrum plotted as a function of a measured energy signal, according to one implementation.

To overcome the additional time and effort required by many-source calibration methods, the methods described herein leverage the fact that PET scanners can be fabricated using lutetium-based scintillators. Lu-176 present in the scintillators provides a source of background radiation that can be used for calibration and/or daily quality control. Using the Lu-176 background spectrum for energy nonlinearity calibration could replace routine energy nonlinearity calibration using multiple isotopes. FIG. 4 shows a plot of the Lu-176 background spectrum as a function of the corrected total energy. As can be seen, the Lu-176 background spectrum has a significant amount of structure. Accordingly, one approach for nonlinearity calibration is to use fitting techniques to determine parameter values (some of which would describe the nonlinearity) that give the best match between the measured spectrum and a parameterized model.

Figure 5:
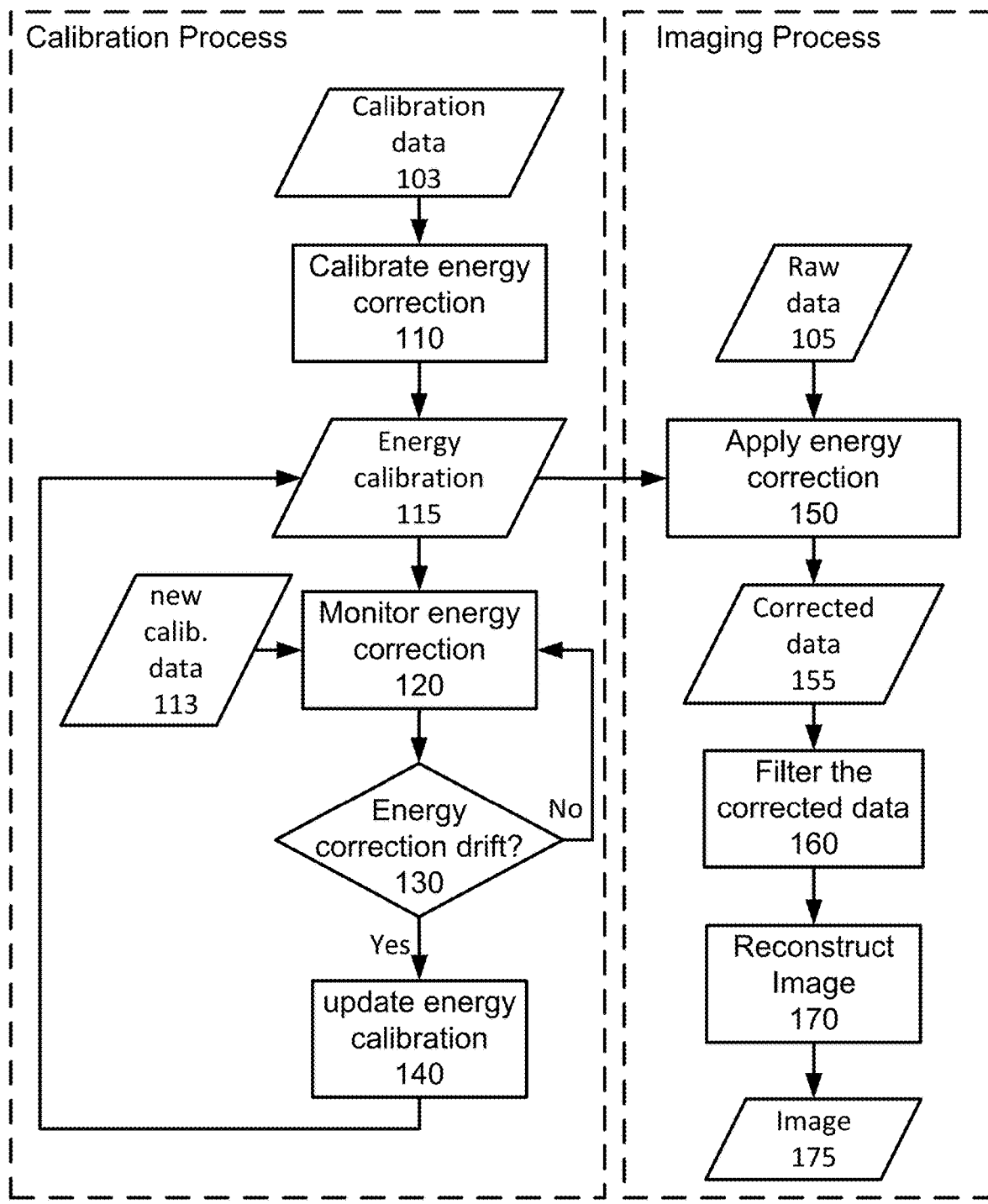
FIG. 5 shows a flow diagram for a method 100 for performing an energy calibration and reconstructing a positron emission tomography (PET) image, according to one implementation.

FIG. 5 shows a flow diagram of method 100, which includes a first process for generating an energy calibration 115 and a second process that uses the energy calibration 115 to correct raw data 105. The corrected data 155 is then used to reconstruct an image. The implementation shown in FIG. 5 is one non-limiting example of using the calibration method described herein. Examples, of medical-imaging modalities that use the corrected data 155 to reconstruct an image include PET and SPECT imaging. Additionally, in other implementations, method 100 can be used for projection imaging, in which case method 100 can omit step 170 and the output becomes a projection image based on the corrected data 155 after filtering at step 160. An example of a medical-imaging modality that would use this other implementation is single photon emission using gamma rays for projection imaging. Further, projection imaging can be performed using any gamma-ray source together with an array of gamma-ray detectors configured as a gamma camera.

In step 110, calibration data 103 is used to generate an energy calibration 115. To ensure that the energy calibration 115 is not underdetermined, the number of spectral features provided by the calibration data 103 should be greater than or equal a number of unique parameters in the energy calibration 115. For example, the energy calibration 115 can be expressed as $$E = f(x,p) = \alpha(\beta + e^{x/\gamma}),$$

wherein E are the calibrated energies, x are the raw energy signals (here these are illustrated as TOT values, which is non-limiting example of the raw energy signals), and p={α, β, γ} are the parameters defining the energy calibration 115. The parameters p can be solved for by defining an objective function (e.g., a least square objective function or a log-likelihood objective function), and solving for the parameters p values that optimized the objective function, achieving agreement between the calibrated energies derived using the energy calibration 115 and known energy values for the spectral features.

In one implementation, step 110 is performed by finding the parameters p that solve the following optimization problem $$\hat{p} = \underset{p}{\mathrm{argmin}}\left\{\sum_i \|E_i^{(c)} - f(x_i^{(c)}, p)\|^2\right\},$$

wherein $E_i^{(c)}$ are known energy values for the spectral features that are to be identified within the calibration spectra in the calibration data 103 and $x_i^{(c)}$ are the raw energy signals for the spectral feature. For example, when the spectral features are the peaks at 202 keV and 307 keV, which can be seen in FIG. 4, then the raw energy signals can be derived by finding the raw energy values in a calibration spectrum of Lu-176 for the local maxima that respectively correspond to these two peaks. When the spectral feature is an edge, such as the edge at 597 keV, then the problem of deriving the raw energy signal corresponding to the edge becomes slightly more involved than determining a local maximum.

Regarding the edge at 597 keV, one approach to determining the raw energy signals for the 597 keV edge uses a physics-based model, for which details are provided below, to fit the shape of the Lu-176 calibration spectrum for the range of values over a predetermined range of energies (e.g., a range of energies from 550 keV to 1 MeV). As discussed below, the 597 keV corresponds to beta replica 8. Further, beta replicas 5-7 can also contribute significantly in the range of 550 keV to 1 MeV, whereas, in this energy range, the contributions of other beta replicas can be insignificant. Given a value for the spectral resolution, which can be determined based on the shapes of the 202 keV and 307 keV peaks, the spectral shapes of these beta replicas can be pre-calculated. Then a simulated spectrum can be calculated by adjusting the weighted sum of the pre-calculated spectral shapes for the beta replicas and translating the summed spectrum along the raw energy signal axis to achieve the best fit between the simulated spectrum and the Lu-176 calibration spectrum. The raw energy signal for the 597 keV edge is provided by the optimal position for the simulated spectrum along the raw energy signal axis.

Other approaches can also be used obtain the raw energy signal corresponding to a third spectral feature. For example, a value between peaks could be used as the third spectral feature. Alternatively, the local maximum near the 597 keV edge can be used as the third spectral feature, or the third spectral feature can be the value near 800 keV at which the Lu-176 spectrum decreases to half the peak value of the local maximum near the 597 keV edge.

In certain implementations, rather than performing calibration using only a few discrete spectral features within the Lu-176 calibration spectrum, the entire Lu-176 calibration spectrum can be used for calibrations. For example, once the detector nonlinearity has been calibrated, a histogram of counts as a function of energy can be stored in memory. Then, when the detector is to be recalibrated (e.g., due to aging and drift in the detector's performance), then the stored histogram can be recalled from memory and compared to a new histogram of the Lu-176 calibration spectra. By adjusting the parameters of the energy calibration 115 until the new calibrated histogram matches the old calibrated histogram, the energy calibration 115 can be periodically fine-tuned to account for changes over time in the nonlinear detector response.

As evidenced by the above example, several variations can be used in step 110 to generate an energy calibration 115 from the calibration data 103. In addition to the above approaches, a four parameter energy calibration 115 can be generated by expanding the calibration data 103 to include a spectrum from another radioactive isotope in addition to Lu-176. For example, the calibration data 103 can include a spectrum from germanium isotope (Ge-68) or fluorine isotope 18 (F-18).

Figure 6:
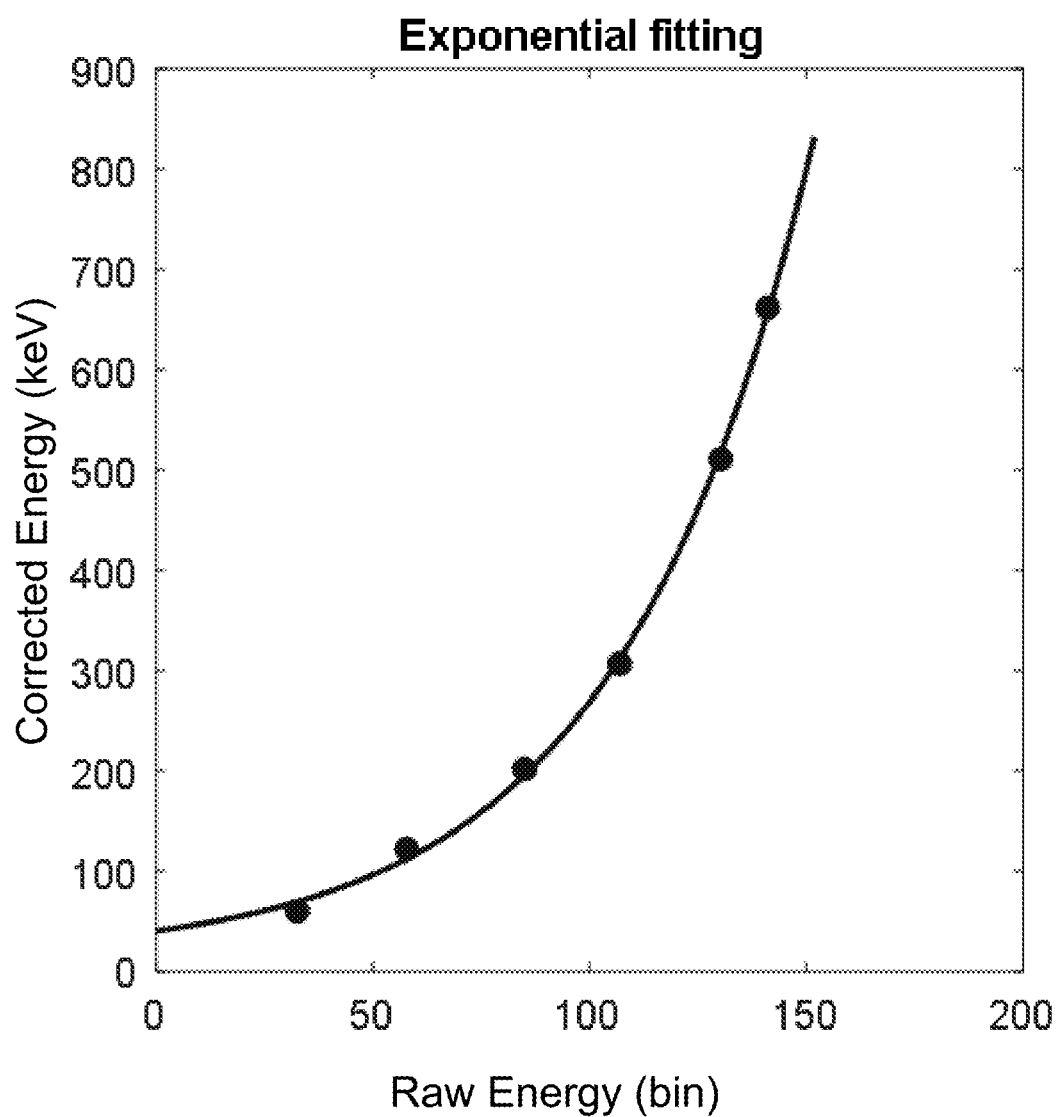
FIG. 6 shows a plot of an energy-calibration model being curve fit to energy calibration data, according to one implementation.

FIG. 6 shows an example of energy-calibration model directed to correcting for the nonlinearity in the Time-over-Threshold (TOT) technique, in which six spectral features were used for the curve fit. In this case, the functional form selected to fit the data is $$E = \alpha(\beta + e^{x/\gamma}).$$

The method 100 is not limited to the energy-calibration model having the particular functional form provided above. In other implementations, the target data can take other forms without departing from the spirit of the invention.

As discussed above, step 110 can also be performed using a multi-source calibration method, and step 140 in which the energy calibration 115 is performed using the approach described above in which only the Lu-176 calibration spectrum is used, or at most the Lu-176 calibration spectrum is used in combination with the spectrum from one other radioactive isotope.

When multi-source calibration is used in step 110, the calibration can be performed using spectra from the following radioactive sources: (i) Am-241 (peak at 59.5 keV), (ii) Ba-133 (peaks at 81 and 356 keV), (iii) Co-57 (peak at 122 keV), (iv) Lu-176 (peaks at 202 and 307 keV), (v) Ge-68 (peak at 511 keV), and (vi) Cs-137 (peak at 662 keV). These isotopes where chosen to cover the range of interest of the 511 keV gamma rays and their Compton-scatter interactions. In a many-source approach to energy calibration, the parameters p of the energy-calibration model f are generated by curve fitting the TOT values corresponding to the 8 energy peaks with respective to the known energies (i.e., 59.5, 81, 122, 202, 307, 356, 511, and 662 keV) for the above-noted isotopes.

In step 120, new calibration data 113, which includes a Lu-176 spectrum is used to monitor whether the nonlinear response of a given detector has changed enough that recalibration is desired. For example, the new calibration data 113 can be accumulated whenever the detector is not being used for imaging (i.e., is in an idle state). Then the energy calibration 115 can be applied to the new calibration data 113, and the calibrated energy value for one of the spectral features in the Lu-176 spectrum can be derived from the energy-corrected Lu-176 spectrum. If the spectral feature being monitored is the 307 keV peak, then the corrected energy value can be determined for the local maximum corresponding to the 307 keV peak. If this corrected energy value differs from the known value (i.e., 307 keV) by more than a predefined threshold, then, in step 130, method 100 signal that "yes" the energy correction has drifted and method 100 proceeds to step 140 to update the energy calibration 115. Otherwise, method 100 continues monitoring new calibration data 113 acquired in between image acquisition.

To avoid, the case that one noisy measurement can result in unnecessarily updating the calibration, the criteria used in step 130 can be based on a moving average or the n out of m of the most recently generated corrected energy values from step 120 are different from the known value by an amount greater than the predefined threshold. For example, if 3 out of 5 times step 120 produces a result outside of the predefined threshold, then proceed to step 140 and update the calibration.

In certain implementations, step 120 can monitor the corrected energy values of multiple spectral features. Whereas monitoring a single spectral feature would be sufficient for a linear energy correction, for a nonlinear energy correction, even though the corrected energy for one spectral feature is accurate, the corrected energy for another spectral feature might be inaccurate. Accordingly, in step 120, the corrected energy values for two or more spectral features can be monitored. Additionally/alternatively, step 120 can monitor a difference between the corrected energy values for two spectral features.

In step 140, the energy calibration 115 and be recalibrated using the above-discussed approaches based on the Lu-176 spectrum and the spectrum of at most one other radioactive isotope.

In step 150, the energy calibration 115 is applied to the raw data 105 to generate corrected data 155. For example, the parameters p are applied together with energy signals x (also referred to as energy coordinates) as inputs to the energy-calibration model f to generate calibrated energy values $E = f(x, \vec{p})$.

Generally, the shape of the nonlinear response will be similar among detector elements/channels, albeit with some variations. To account for these variations, the parameters can be calibrated for each readout channel/module.

As discussed above, the energy-calibration model f is not limited to a functional form of $$E = f(x, \vec{p}) = \alpha(\beta + e^{x/\gamma}).$$

For example, as an alternative to a functional-form parameterization, the parametrization can be expressed using parameters in a Look-Up-Table (LUT). In one implementation, e.g., a LUT can relate discrete points for the mapping $E_i = f(x_i)$, and interpolation can be used to determine the mapping for points in between the discrete points.

Accordingly, in certain implementations, rather than using a functional form, the nonlinearity correction can be specified by a LUT, in which the LUT specifies correction factors corresponding to specific signal levels. Correction factors for signal levels which do not appear in the LUT can be determined by interpolation or extrapolation from values which do appear in the LUT. Different methods of interpolation (e.g. spline, linear, or cubic) can be used depending on accuracy and computational complexity constraints. Similarly, the number of signal levels in the LUT can depend on the accuracy and computational complexity constraints. Generally, a larger number of values will result in improved energy resolution (i.e., accuracy of correction). For the case of a LUT approach, every correction factor in the LUT can be a respective parameter that is determined by the energy calibration.

As discussed above, the energy calibration can include TOT nonlinearity corrections, but is not limited to TOT nonlinearity corrections. Additionally, the energy calibration can account for nonlinearities due to charge sharing, thresholding, and other nonlinear effects. Further, the energy calibration can be a lookup table indexed by the positions/identities (IDs) of respective detector elements to obtain parameters of an equation expressing a nonlinear correction. Accordingly, the parameterization of the energy calibration can be performed on a detector element by detector element basis.

At step 160, an energy window is applied to the corrected to remove random coincidences and thereby improve the image quality. For example, in PET imaging the energy window will span the 511 keV energy corresponding positron annihilation. As discussed above, in certain implementations, multi-channel detections can be salvaged by discriminating which detection events correspond to multi-channel events, and then summing the energies for respective multi-channel detections to determine the total energy for each multi-channel detection event. Details for one implementation of this process are provided below.

At step 170, a PET image 155 is reconstructed from the correct PET data using any known reconstruction method. For example, the PET data 145 can be used to reconstruct an image of radioactivity level (e.g., tracer density) as a function of voxel position. The image reconstruction can be performed using a back-projection method, a filtered back-projection method, a Fourier-transform-based image reconstruction method, an iterative image reconstruction method, a matrix-inversion image reconstruction method, a statistical image reconstruction method, a list-mode method, or other reconstruction method or combination thereof, as would be understood as a person of ordinary skill in the art. For example, the 1 PET image 175 can be reconstructed using an ordered subset expectation maximization (OS-EM) algorithm that is initialized with an FBP reconstructed PET image.

Returning to step 160, the raw data 105 can include energies, times, and positions corresponding to gamma-ray detection events. For example, the detection events can correspond to pairs of gamma rays emitted during a positron-electron annihilation event occurring in an object OBJ. The detection events can be detected at any one of a plurality of detector elements. When multi-channel detection occurs, the energy from a single gamma ray is distributed and detected among two or more detector elements. These two or more detector elements can be within a single detector module (e.g., adjacent detector elements), or can be distributed among two or more detector modules. For example, in Compton scattering, the scattered gamma ray can traverse several detector elements before being absorbed in a second detector element far from the first detector element at which Compton scattering occurred.

At step 160, the multi-channel detection events are identified from the energy corrected data 155 multi-channel detection events, and then the identified multi-channel detection events are grouped by event. That is, each of the groups corresponds a single primary gamma ray. For first-order scatter, each group will include two hits: one hit being the energy detected in the first crystal at which Compton scattering occurred, and the other being the energy detected in the second crystal at which the scattered gamma ray is absorbed via the photoelectric absorption. Similarly, each group for a second-order scatter event will include three hits (i.e., one for the primary gamma ray and two for each of the two scattered gamma rays), and so forth (e.g., four hits in groups corresponding to third-order scatter, etc.).

Multi-channel events can be selected, e.g., based on the detection signals' proximity in time, based on the detection signals' proximity in space, based on the sum of the energies of the signals, or based any combination thereof. For example, if the gamma-ray source has a known energy (e.g., 511 keV for gamma rays from positron annihilation), then the more closely the signals sum to the known energy the more likely the signals correspond to a same multi-channel event. Further, signals occurring closer together in time are more likely to correspond to a same multi-channel event, and signals occurring closer together in space are more likely to correspond to a same multi-channel event. Moreover, when all three of the above conditions (i.e., energy, time, and space) are all satisfied, then the signals are even more likely to correspond to a same multi-channel event. Thus, the processing to group signals into multi-channel events can be performed using a multivariate statistical analysis.

As discussed above, in certain implementations, the energy signal values of various spectral features can be determined using a physics-based model of the spectrum. In this approach, the input spectrum is fit to a complex physics-based model of the spectrum. The model includes adjustable parameters to describe the nonlinearity. The best-fit to the data provides, among other parameters, the nonlinearity coefficients.

Figure 7:
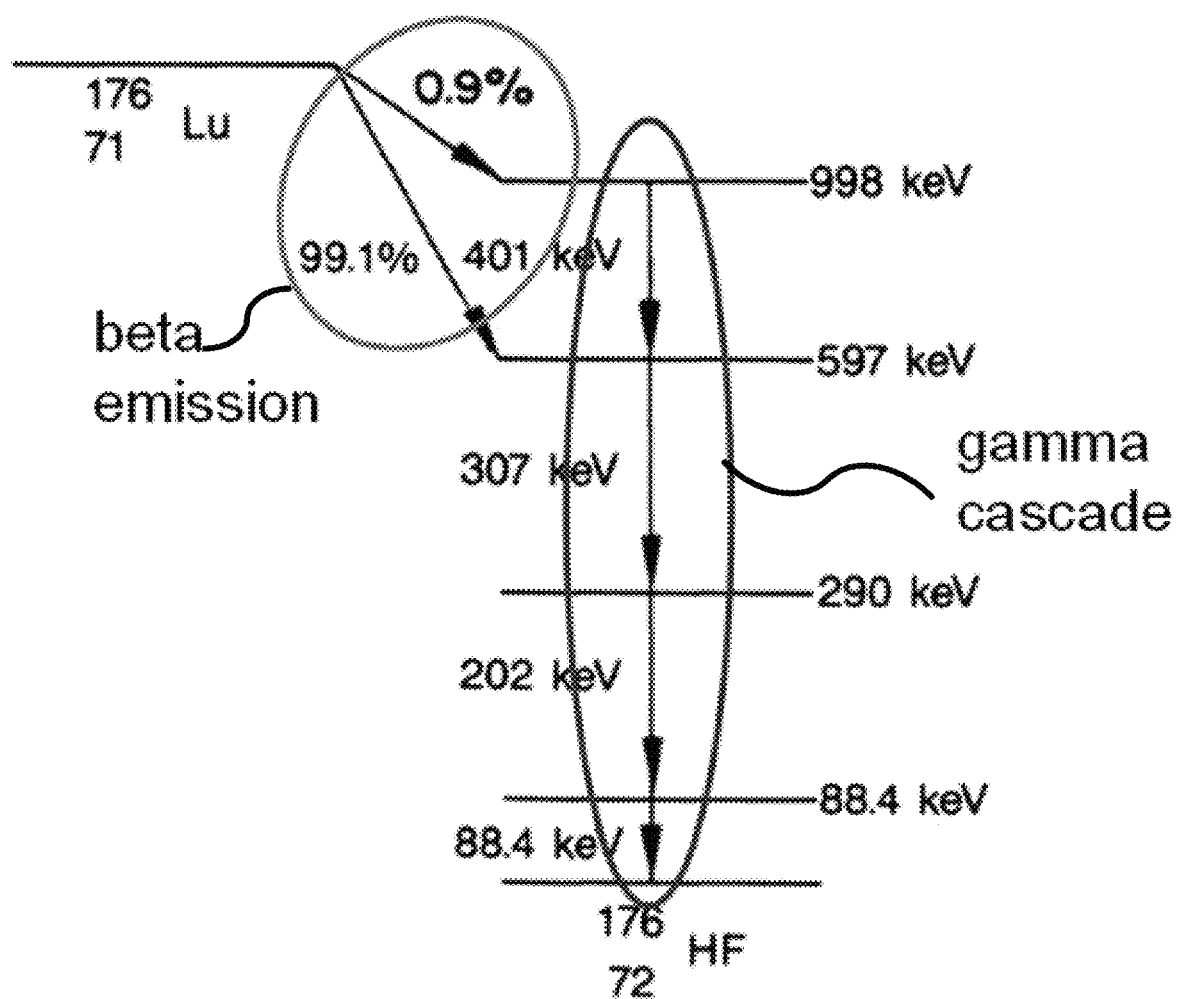
FIG. 7 shows a diagram of an energy level diagram of Lu-176 for a physics-based model of the Lu-176 spectrum, according to one implementation.
Figure 8:
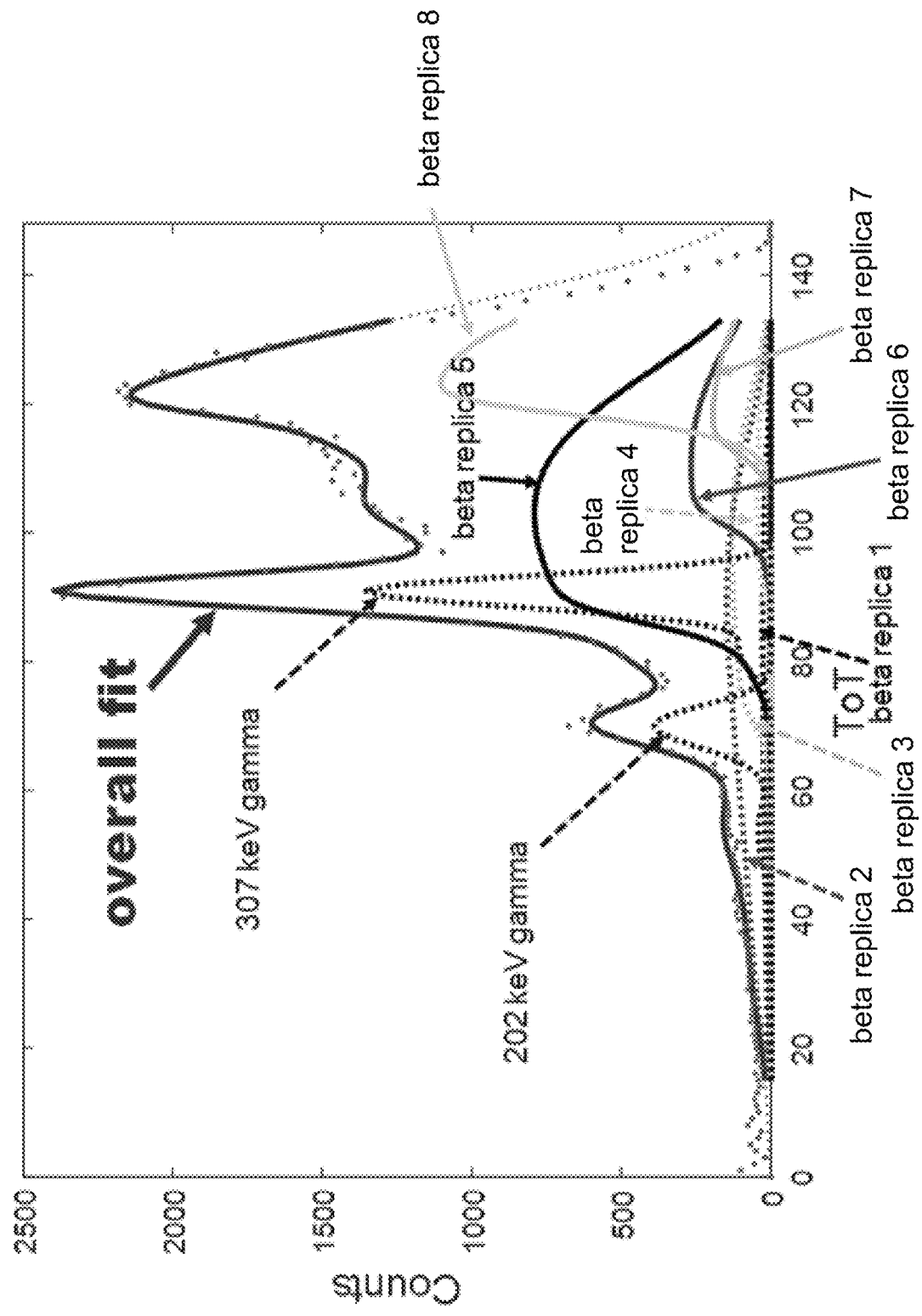
FIG. 8 shows a plot of spectra for respective decay pathways/radiation processes that contribute to the Lu-176 spectrum, according to one implementation.

FIG. 7 shows a level diagram for the energy levels and radiation pathways in Lu-176. As shown in FIG. 7, Lu-176 decays by beta emission followed by a cascade of gamma rays. The beta emission and gamma cascade essentially occur simultaneously (i.e., they occur much closer in time than the resolution of the detector system). FIG. 8 shows that, based on the physical model, the Lu-176 spectrum can be modeled as a superposition of spectra from several contributing radiative decay processes.

In view of FIGS. 7 and 8, the physics-based model can be better understood by considering several simplifying assumptions. First, in the beta emission, it can be assumed that all decays occur through the 99.1% path.

Second, the beta energy is essentially always fully captured in the scintillator. Thus, it can be assumed that 100% of beta particles deposit all of their energy in the crystal in which they originate.

Third, the gamma rays (88, 202 and 307 keV) may either be captured or they may escape. The probability depends on the energy and the scintillator size. Consequently, the beta spectrum gets replicated several times, and the overall spectrum is the sum of these replicated spectra. For example, the decays for which the 88 keV and 307 keV gamma rays are captured produce a beta spectrum which is shifted by (88+307=395 keV). Accordingly, it can be assumed that the probability of escape for each of the three gamma rays can be represented by three probabilities (P88, P202, P307), wherein P88 is the probability that the 88 keV gamma ray escapes, P202 is the probability that the 202 keV gamma ray escapes, P307 is the probability that the 307 keV gamma ray escapes, and P88<P202<P307. This is a simplification because, in reality, the probability of escape depends on the location at which the radiative decay occurs within the scintillator, whereas here it is assumed that the probability of escape is a constant, rather than a function of position and geometry of the crystal.

TABLE 1 probabilities of the eight beta replica scenarios.

| num | 88 keV captured | 202 keV captured | 307 keV captured | 1st order replica relative amplitude |
|---|---|---|---|---|
| 1 | — | — | — | P88*P202*P307 |
| 2 | X | — | — | (1 − P88)*P202*P307 |
| 3 | — | X | — | P88*(1 − P202)*P307 |
| 4 | — | — | X | P88*P202*(1 − P307) |
| 5 | X | X | — | (1 − P88)*(1 − P202)*P307 |
| 6 | X | — | X | (1 − P88)*P202*(1 − P307) |
| 7 | — | X | X | P88*(1 − P202)*(1 − P307) |
| 8 | X | X | X | (1 − P88)*(1 − P202)*(1 − P307) |

Fourth, for three gamma rays, each of which can escape or be captured, there are $2^3=8$ possible beta spectrum replicas. For each of the eight possible permutations according to which the three gamma rays do or do not escape, the probability is given in Table 1. The beta replica number on the left-hand-side corresponds to the beta replica number shown in FIG. 8. For example, if both the 88 keV and 202 keV gamma rays are captured, then the spectrum will be shifted (i.e., 88+202=290 keV), providing the spectrum for beta replica 5 as shown in FIG. 8. Further the probability (weight) given to this scenario is given by (1−P88)*(1−P202)*P307.

Fifth, in the presence of other scintillator elements (such as other scintillator pixels in the same detector block or other detectors in a PET detector ring), the escapes from one detector (mainly 202 and 307 keV) can be detected in other detectors, resulting in additional peaks. To simplify the physical model it can be assumed that only the 202 and 307 keV escapes from other detector elements result in significant contributions to the overall spectrum.

Sixth, the features of the spectrum will be modified by the energy resolution of the overall detection system (combination of scintillator, photosensor, and electronics). To simplify the physical model it can be assumed that the energy resolution can be described by a single parameter. For example, the resolution at 511 keV ($E_{res}^{(511\ keV)}$) can be used as the one parameter, and it can be assumed that the energy resolution at a given energy, E, is given by $$E_{res}(E) = E_{res}^{(511keV)} \times \sqrt{\frac{E}{511\ \text{keV}}}.$$

Above, the energy resolution is assumed to scale with the square-root of the energy.

Each of the beta replicas can be represented by a parameterized shape function B, which is expressed as B($E_{00}$, $E_{res}^{(511\ keV)}$), wherein $E_{00}$ is the energy shift of the replica due to the simultaneously absorbed gamma rays. The amplitude is determined by an amplitude scale factor, A, and the relative amplitude factor, which is provided in the right-most column in Table 1. As an example, for the replica representing line 6 in Table 1 (i.e., the gamma rays of energy 88 and 307 keV are captured), the energy shift is $E_{00}$=88+307=395 keV, and the overall replica for beta replica $6\beta_6$ would be $$\beta_6 = A \times (1-P88) \times P202 \times (1-P307) \times B(395, E_{res}^{(511\ keV)}).$$

The overall energy spectrum is the sum of 8 beta-replicas and two gamma peaks (202 and 307 keV) resulting from absorption of escapes from other detector elements, as shown in FIG. 8. Additional equations can be applied to model the effects of links along the detection pathway (e.g., scintillators, photosensors, and read-out electronics). For example, the quantum efficiency of the photosensors might vary as a function of energy.

Next, the nonlinearity of the detector is represented by parameterized equations. For example, for a detector read-out using the Time-over-Threshold (ToT) method, four parameters—C, a, E0, and ToT511—can be used to describe the nonlinearity. The energy, E, is then represented by the equations:

$$d = E0/C - 1,$$

$$b = \text{ToT}511/\log(511/C - d);\ \text{and}$$

$$E = C^*(\exp(\text{ToT}/(a/\text{ToT}+b))+d),$$

wherein ToT is the measured signal.

Putting all of the above assumption together, the overall Lu-176 spectrum is described by a physical model with 11 free parameters:

| 1 | A: | overall scaling factor for beta-replicas |
| 2 | Eres_511: | energy resolution at 511 keV |
| 3 | P88: | 88 keV escape probability |
| 4 | P202: | 202 keV escape probability |
| 5 | P307: | 307 keV escape probability |
| 6 | A202: | amplitude of 202 keV peak (escapes from other detectors) |
| 7 | A307: | amplitude of 307 keV peak (escapes from other detectors) |
| 8 | C | nonlinearity parameter #1 |
| 9 | a: | nonlinearity parameter #2 |
| 10 | E0: | nonlinearity parameter #3 |
| 11 | ToT511: | nonlinearity parameter #4 |

This number of free parameters can be reduced when the only question is what energy signal value corresponds to the 597 keV edge. For example, the values for A202 and A307 can be ignored, and the value Eres_511 can be obtained from the 202 keV and 307 keV peaks. Further, a two parameter fit, rather than the four parameter fit can be used to scale and translate the ToT value ToT with respect to the energy value E, reducing the number of free parameters to six. These six parameters can be determined by fitting methods known to those skilled in the art. For example, they can be determined using a simplex search, or they can be determined using a least-squares penalty function.

Figure 9A:
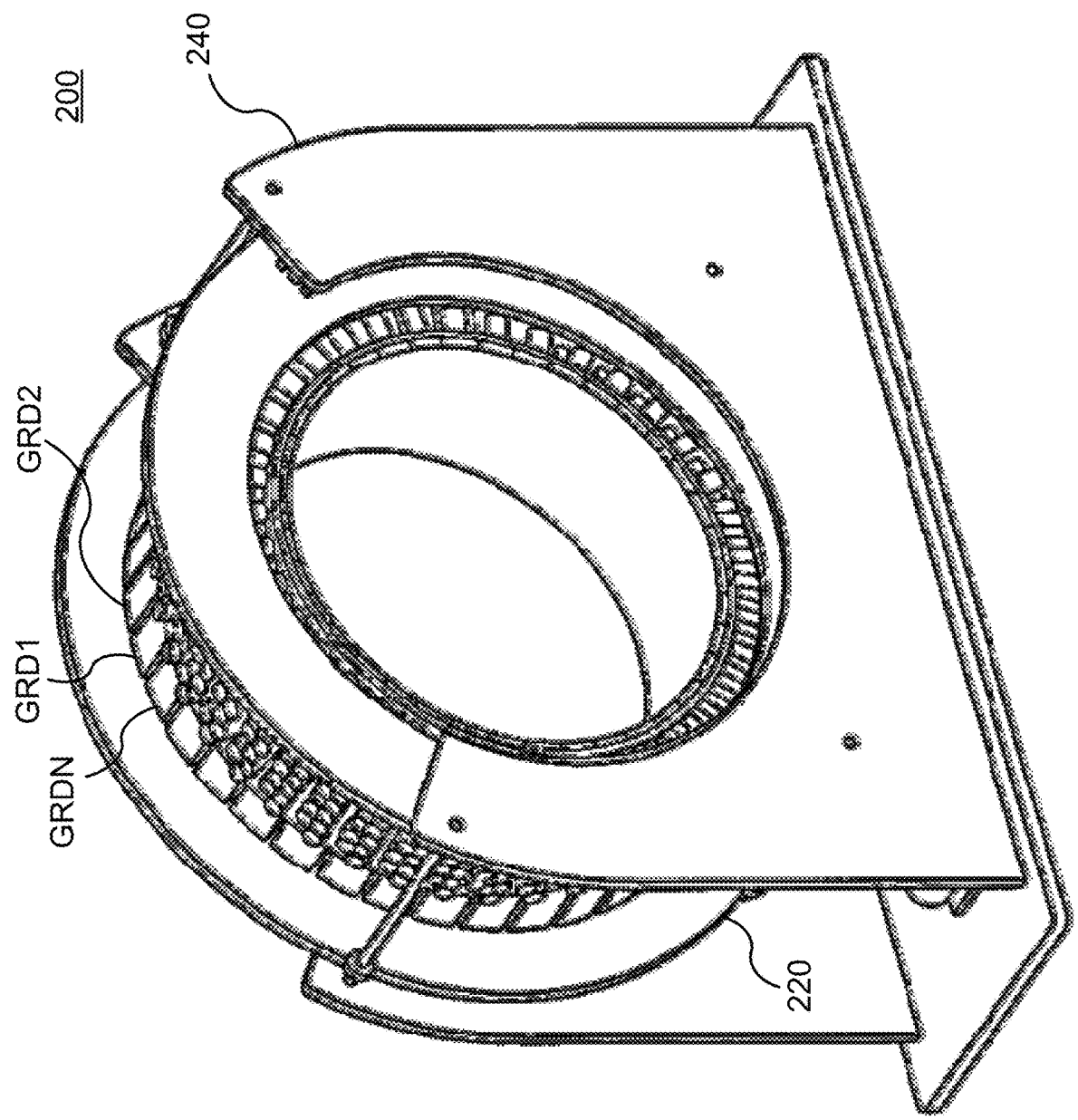
FIG. 9A shows a perspective view of a PET scanner, according to one implementation.
Figure 9B:
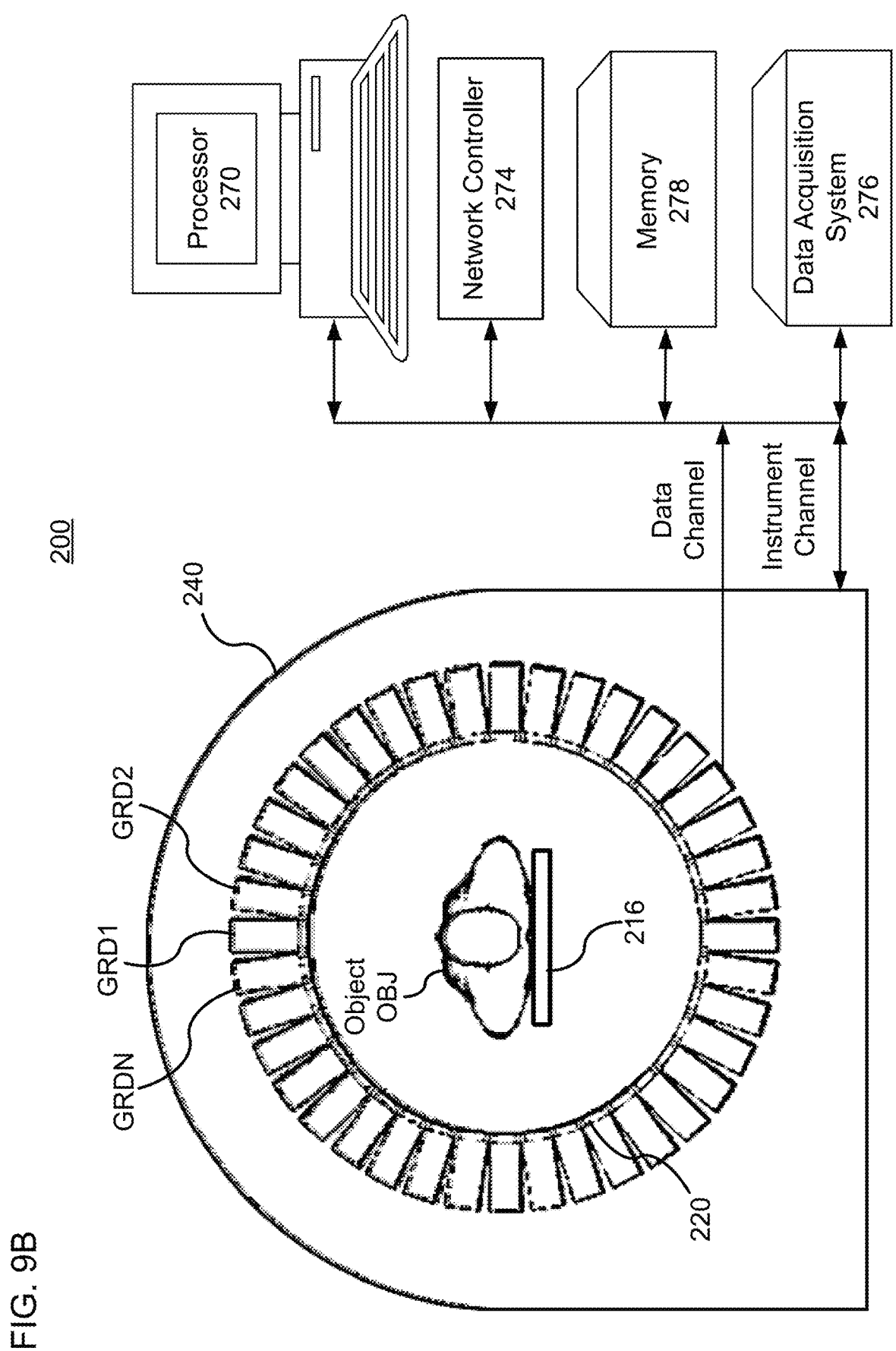
FIG. 9B shows a schematic view of the PET scanner, according to one implementation.

FIGS. 9A and 9B show a non-limiting example of a PET system 200 that is configured with detector modules (i.e., gamma-ray detectors (GRD)) arranged in an annular shape. Each of the detector modules can include several arrays of detector elements. The GRDs include scintillator crystal arrays for converting the gamma rays into scintillation photons (e.g., at optical, infrared, and ultraviolet wavelengths), which are detected by photodetectors. In the non-limiting example illustrated in FIGS. 9A and 9B, the photodetectors are photomultiplier tubes (PMTs) that are much bigger than the respective scintillator crystal elements. In one preferred embodiment, the photodetectors are silicon photomultipliers (SiPMs) that can have a detection cross-section that approximates the cross-sectional area of the individual scintillator crystal elements, creating a one-to-one correspondence between the crystals and the photodetectors. If the photodetectors are larger than the crystals, such that a single photodetector is used to detect the optical signals from multiple crystals, then Anger arithmetic can be used to determine the positions. However, Anger arithmetic is not necessarily required when there is a one-to-one correspondence between the crystals and the photodetectors.

FIGS. 9A and 9B show a non-limiting example of a PET scanner 200 that can implement the methods 100 and 160. The PET scanner 200 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 200.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 9B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 9A and 9B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 9B shows an example of the arrangement of the PET scanner 200, in which the object OBJ to be imaged rests on a table 216 and the GRD modules GRD1 through GRDN are arranged circumferentially around the object OBJ and the table 216. The GRDs can be fixedly connected to a circular component 220 that is fixedly connected to the gantry 240. The gantry 240 houses many parts of the PET imager. The gantry 240 of the PET imager also includes an open aperture through which the object OBJ and the table 216 can pass, and gamma-rays emitted in opposite directions from the object OBJ due to an annihilation event can be detected by the GRDs and timing and energy information can be used to determine coincidences for gamma-ray pairs.

In FIG. 9B, circuitry and hardware is also shown for acquiring, storing, processing, and distributing gamma-ray detection data. The circuitry and hardware include: a processor 270, a network controller 274, a memory 278, and a data acquisition system (DAS) 276. The PET imager also includes a data channel that routes detection measurement results from the GRDs to the DAS 276, a processor 270, a memory 278, and a network controller 274. The data acquisition system 276 can control the acquisition, digitization, and routing of the detection data from the detectors. In one implementation, the DAS 276 controls the movement of the bed 216. The processor 270 performs functions including reconstructing images from the detection data, pre-reconstruction processing of the detection data, and post-reconstruction processing of the image data, as discussed herein.

The processor 270 can be configured to perform various steps of methods 100 and 160 described herein and variations thereof. The processor 270 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 270 can execute a computer program including a set of computer-readable instructions that perform various steps of methods 100 and 160, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 278 can be a hard disk drive, CD-ROM drive, DVD drive, FLASH drive, RAM, ROM or any other electronic storage known in the art.

The network controller 274, such as an Intel Ethernet PRO network interface card from Intel Corporation of America, can interface between the various parts of the PET imager. Additionally, the network controller 274 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 10:
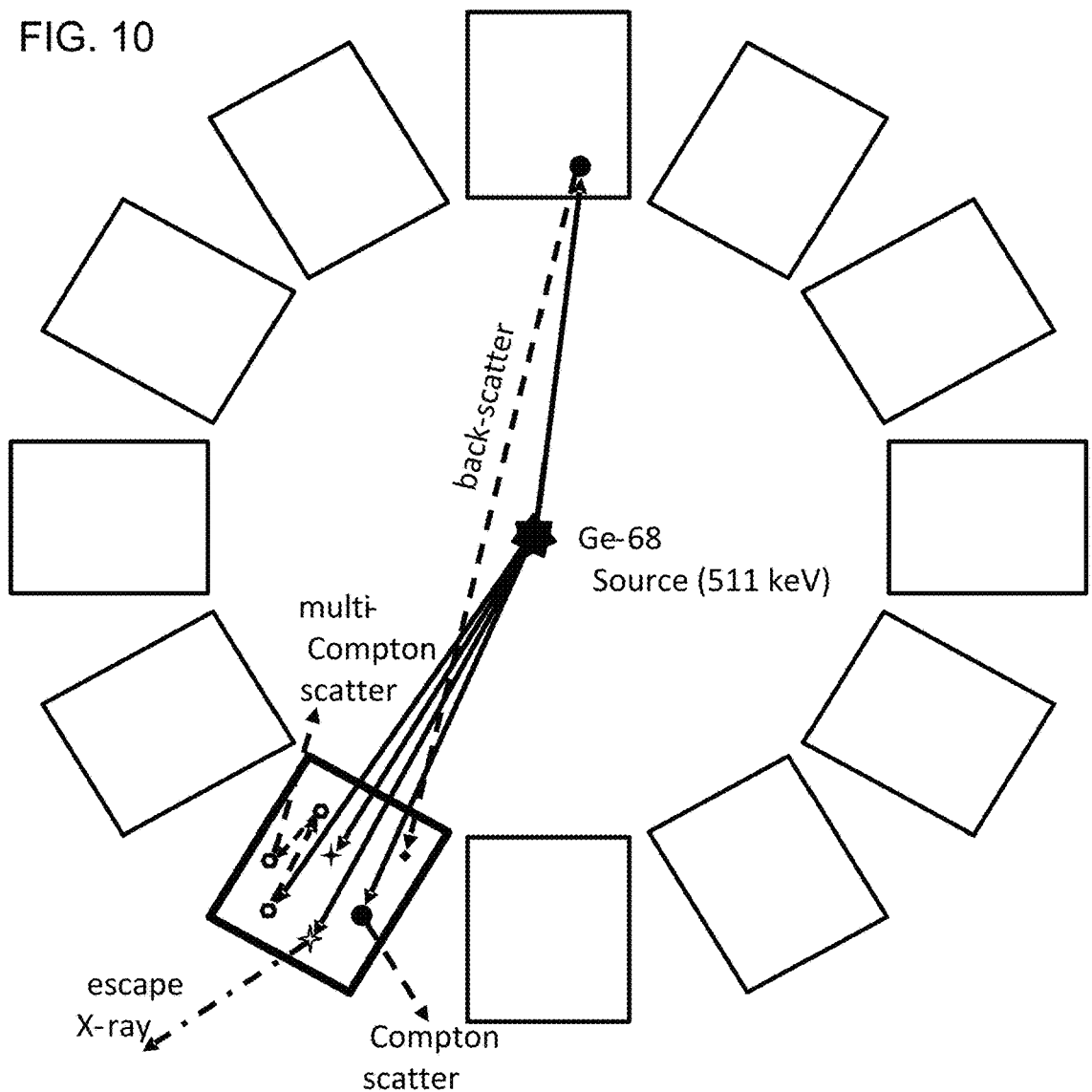
FIG. 10 shows a schematic diagram of scattering processes in an imaging scanner in the presence of a radiation source emitting radiation of a single energy, according to one implementation.
Figure 11A:
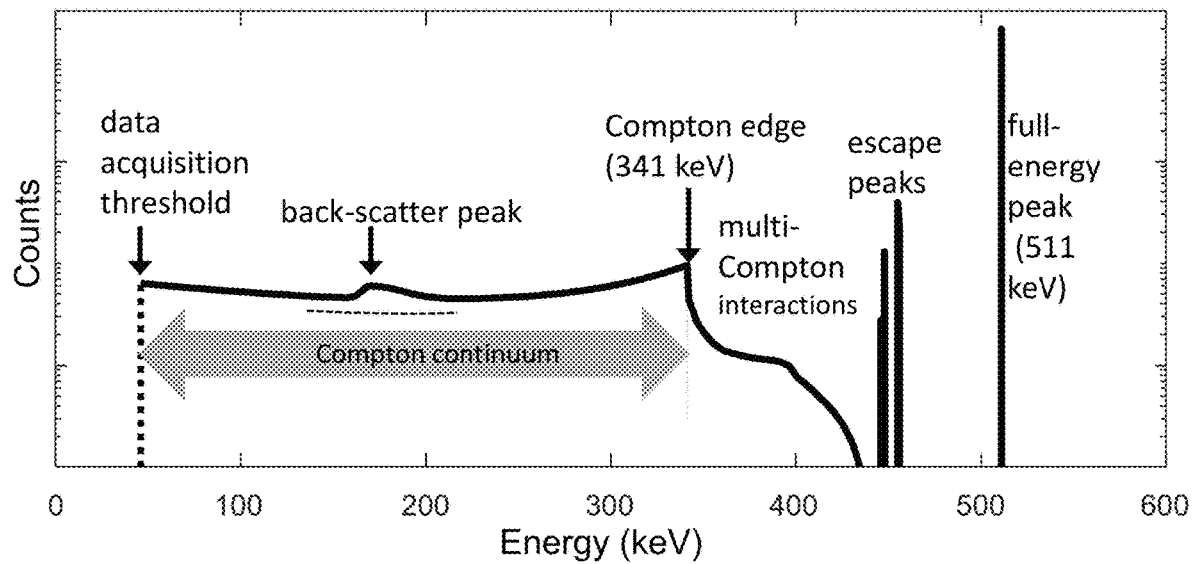
FIG. 11A shows a plot of absorbed radiation contributed to by the various scattering processes represented in FIG. 10, when the detector has perfect energy resolution.
Figure 11B:
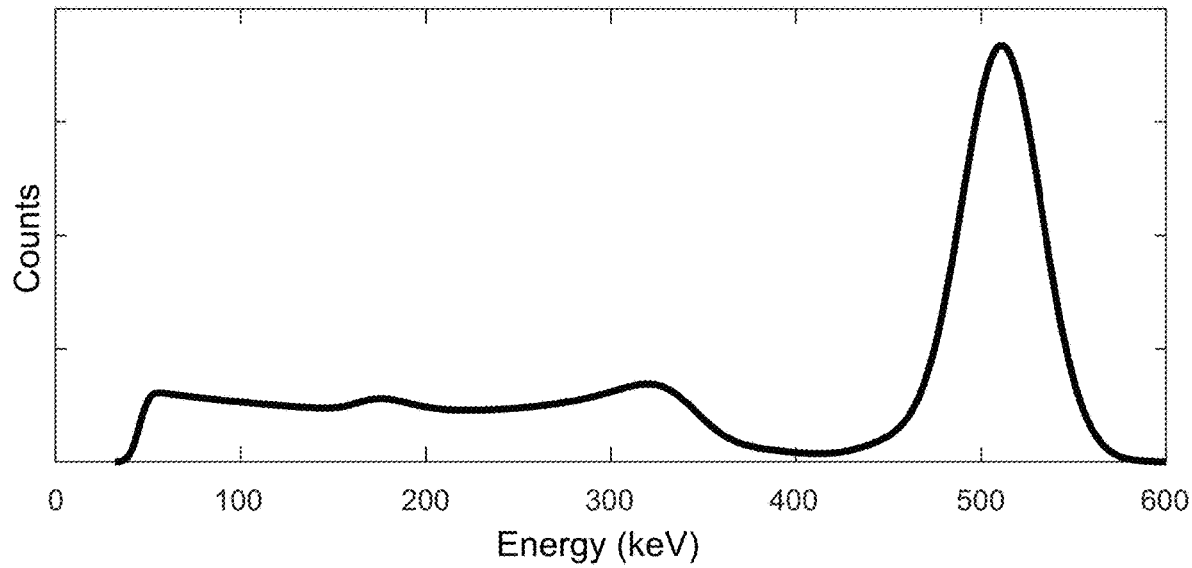
FIG. 11B shows a plot of absorbed radiation contributed to by the various scattering processes represented in FIG. 10, when the detector has finite energy resolution.

The above implementations, of method 100 are illustrated mostly using spectra of Lu-176. The Lu-176 spectra are advantageous for non-linear energy calibrations because they exhibit numerous discrete and continuous spectral features. However, spectra from single-peak spectra such as Ge-68 can also generate discrete and continuous spectral features due to Compton scattering and other physical processes in the detector crystals. That is, as a practical matter, the spectrum of radiation absorbed at a detector can have additional features (e.g., a back-scatter peak and a Compton edge) beyond those in the emission spectrum of the radioisotope. These additional features can include a Compton back scatter peak, a Compton edge, and various escape peaks, as illustrated in FIGS. 10, 11A, and 11B. Thus, a radioisotope with only a single emission energy can be used calibrate multiple spectral features and therefore perform an nonlinear energy calibration.

FIG. 10 shows a schematic diagram of various physical processes arising from a single-energy radiation source. Here, Ge-68 emits gamma rays at 511 keV. However, backscatter from the crystal at the top of the ring is shown being absorbed by the detector in the lower left region of the ring. Further, FIG. 10 shows gamma ray energy being absorbed due to multi-Compton scattering and energy being absorbed in the presence of X-ray escape. FIG. 11A shows an absorption spectrum arising from the detection of 511 keV gamma rays emitted from Ge-68, including various spectral features corresponding to the above-noted scattering processes. In FIG. 11A, a logarithmic scale is used for the vertical and the absorption spectrum is illustrated under the assumption of perfect detector resolution in order better resolve the various features. In FIG. 11B, a linear scale is used for the vertical axis, and a finite detector resolution is assumed. Even though, Ge-68 emits gamma rays having only a single energy, the absorbed energy shows many different spectral features (e.g., due to the back-scatter peak and the Compton edge). Thus, even when the radiation source emits only a single energy of radiation, the detection process can result in many spectral features. In view of this, the methods described herein can be used with spectra from radiation sources like Ge-68, which emit radiation at a single energy, in addition to being used with radiation sources like Lu-176, which emit radiation at multiple energies.

A physics-based model of the various scattering processes shown in FIGS. 20, 11A, and 11B can be applied using known analytical and numerical expressions for the scattering processes. Thus, either the DL network implementation or the physics-based model implementation can be applied to an absorption spectrum obtained from a radiation source emitting at only one or two energies.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A gamma-ray emission imaging apparatus, comprising:
processing circuitry configured to
obtain calibration data of ionizing radiation incident at a detector of a gamma-ray imager, wherein the calibration data comprises a first energy spectrum acquired when the detector is irradiated via radiation from a radioisotope in a scintillator crystal of the gamma-ray imager, and
determine an energy calibration in which first, second, and third energy signals corresponding to first, second, and third spectral features from the first energy spectrum are applied to a nonlinear energy correction to generate first, second, and third calibrated energy signals corresponding to first, second, and third calibrated spectral features having different relative distances on an energy scale between the first, second, and third calibrated spectral features as compared to the first, second, and third spectral features, the energy calibration being performed by adjusting parameters of the nonlinear energy correction to optimize agreement between (1) locations, on the energy scale, of first, second, and third reference spectral features of a reference spectrum that represents absorbed radiation energy and (2) locations, on the energy scale, of the first, second, and third calibrated spectral features, wherein the third reference spectral feature is a sum of the first and second reference spectral features.

2. The apparatus according to claim 1, wherein the processing circuitry is further configured to acquire counts from background radiation emitted from the scintillator crystal during a time between imaging scans during which the gamma-ray imager is not being used for imaging, the acquired counts being the calibration data used to determine the energy calibration.

3. The apparatus according to claim 1, wherein at least one of the first, second, and third reference spectral features is an edge.

4. The apparatus according to claim 1, wherein the radioisotope is lutetium isotope 176 (Lu-176), the first reference spectral feature is a peak at 202 keV, and the second reference spectral feature is a peak at 307 keV.

5. The apparatus according to claim 4, wherein the processing circuitry is further configured to determine the energy calibration using an edge at 597 keV in the reference spectrum as a third reference spectral feature.

6. The apparatus according to claim 1, wherein the processing circuitry is further configured to use an objective function to optimize the agreement between locations, on the energy scale, of the first, second, and third reference spectral features and the locations, on the energy scale, of the first, second, and third calibrated spectral locations, the objective function representing agreement between a reference histogram of the reference spectrum and an energy corrected histogram generated by applying the nonlinear energy correction to the first energy spectrum.

7. The apparatus according to claim 1, wherein the processing circuitry is further configured to:
obtain additional calibration data using the radioisotope, the additional calibration data being acquired after the energy calibration has been determined,
apply the energy calibration to the additional calibration data to determine corrected energies of the first, second, and third spectral features in the additional calibration data, and
signal to update the energy calibration when a difference between locations of the first, second, and third reference spectral features and locations of the first, second, and third spectral features determined using the additional calibration data satisfies a recalibration criterion.

8. The apparatus according to claim 7, wherein the first reference spectral feature is a peak or a valley in the reference spectrum.

9. The apparatus according to claim 1, wherein the processing circuitry is further configured to
obtain emission data from a medical-imaging scan generated using the gamma-ray imager,
filter the emission data to omit counts for which a corrected energy values fall outside an energy window that spans 511 keV, and
reconstruct a tomographic image using the filtered emission data.

10. The apparatus according to claim 9, wherein the processing circuitry is further configured to acquire the emission data using the gamma-ray imager, and the gamma-ray imager is one of a positron emission tomography (PET) scanner and single photon emission computed tomography (SPECT) scanner.

11. The apparatus according to claim 1, wherein the first reference spectral feature is an emission peak of a radiation energy emitted by the radioisotope.

12. A method, comprising:
obtaining calibration data of ionizing radiation incident at a detector of a gamma-ray imager, and the calibration data comprises a first energy spectrum acquired when the detector is irradiated via radiation from a radioisotope in a scintillator crystal of the gamma-ray imager, and
determining an energy calibration in which first, second, and third energy signals corresponding to first, second, and third spectral features from the first energy spectrum are applied to a nonlinear energy correction to generate first, second, and third calibrated energy signals corresponding to first, second, and third calibrated spectral features having different relative distances on an energy scale between the first, second, and third calibrated spectral features as compared to the first, second, and third spectral features, the energy calibration being performed by adjusting parameters of the nonlinear energy correction to optimize agreement between (1) locations, on the energy scale, of first, second, and third reference spectral features of a reference spectrum that represents absorbed radiation energy and (2) locations, on the energy scale, of the first, second, and third calibrated spectral features, wherein the third reference spectral feature is a sum of the first and second reference spectral features.

13. The method according to claim 12, further comprising acquiring counts from background radiation emitted from the scintillator crystal during a time between imaging scans during which the gamma-ray imager is not being used for imaging, the acquired counts being the calibration data used to determine the energy calibration.

14. The method according to claim 12, wherein at least one of the first, second, and third reference spectral features is an edge.

15. The method according to claim 12, wherein the radioisotope is lutetium isotope 176 (Lu-176), the first reference spectral feature is a peak at 202 keV, and the second reference spectral feature is a peak at 307 keV.

16. The method according to claim 15, further comprising determining the energy calibration using an edge at 597 keV in the reference spectrum as a third reference spectral feature.

17. The method according to claim 12, wherein an objective function is used to optimize the agreement between locations, on the energy scale, of the first, second, and third reference spectral features and the locations, on the energy scale, of the first, second, and third calibrated spectral locations, the objective function representing agreement between a reference histogram of the reference spectrum and an energy corrected histogram generated by applying the nonlinear energy correction to the first energy spectrum.

18. A gamma-ray emission imaging apparatus comprising:
processing circuitry configured to
obtain calibration data of ionizing radiation incident at a detector of a gamma-ray imager, and the calibration data comprises a first energy spectrum acquired when the detector is irradiated via radiation from a radioisotope in a scintillator crystal of the gamma-ray imager, and
determine an energy calibration in which first and second energy signals corresponding to first and second spectral features from the first energy spectrum are applied to a nonlinear energy correction to generate first and second calibrated energy signals corresponding to first and second calibrated spectral features having different relative distances on an energy scale between the first and second calibrated spectral features as compared to the first and second spectral features, the energy calibration being performed by adjusting parameters of the nonlinear energy correction to optimize agreement between (1) locations, on the energy scale, of first and second reference spectral features of a reference spectrum that represents absorbed radiation energy and (2) locations, on the energy scale, of the first and second calibrated spectral features, wherein the first reference spectral feature is an emission peak of a radiation energy emitted by the radioisotope, and the second reference spectral feature is a back-scatter peak, a Compton edge, an escape peak, or a beta replica edge.

19. The apparatus according to claim 18, wherein the second spectral feature is a back-scatter peak.

20. The apparatus according to claim 18, wherein the second spectral feature is a Compton edge.

21. The apparatus according to claim 18, wherein the second spectral feature is an escape peak.

22. The apparatus according to claim 18, wherein the second spectral feature is a beta replica edge.

23. A method comprising:
obtaining calibration data of ionizing radiation incident at a detector of a gamma-ray imager, and the calibration data comprises a first energy spectrum acquired when the detector is irradiated via radiation from a radioisotope in a scintillator crystal of the gamma-ray imager, and
determining an energy calibration in which first and second energy signals corresponding to first and second spectral features from the first energy spectrum are applied to a nonlinear energy correction to generate first and second calibrated energy signals corresponding to first and second calibrated spectral features having different relative distances on an energy scale between the first and second calibrated spectral features as compared to the first and second spectral features, the energy calibration being performed by adjusting parameters of the nonlinear energy correction to optimize agreement between (1) locations, on the energy scale, of first and second reference spectral features of a reference spectrum that represents absorbed radiation energy and (2) locations, on the energy scale, of the first and second calibrated spectral features, wherein the first reference spectral feature is an emission peak of a radiation energy emitted by the radioisotope, and the second reference spectral feature is a back-scatter peak, a Compton edge, an escape peak, and a beta replica edge.

24. A gamma-ray emission imaging apparatus comprising:
processing circuitry configured to
obtain calibration data of ionizing radiation incident at a detector of a gamma-ray imager, and the calibration data comprises a first energy spectrum acquired when the detector is irradiated via radiation from a radioisotope in a scintillator crystal of the gamma-ray imager and a second energy spectrum corresponding to an isotope that is external to the scintillator crystal, and
determine an energy calibration in which first and second energy signals corresponding to first and second spectral features from the first energy spectrum are applied to a nonlinear energy correction to generate first and second calibrated energy signals corresponding to first and second calibrated spectral features having different relative distances on an energy scale between the first and second calibrated spectral features as compared to the first and second spectral features, the energy calibration being performed by adjusting parameters of the nonlinear energy correction to optimize agreement between (1) locations, on the energy scale, of first and second reference spectral features of a reference spectrum that represents absorbed radiation energy with respect to the first energy spectrum, (2) locations, on the energy scale, of the first and second calibrated spectral features, and (3) a location on the energy scale of a third reference spectral feature with respect to the second energy spectrum and a location of a third calibrated spectral feature.

25. The apparatus according to claim 24, wherein at least one of the first, second, or third reference spectral feature is an emission peak at an energy selected from the group consisting of: 59.5, 81, 122, 202, 307, 356, 511 and 662 keV.

26. A method comprising:
obtaining calibration data of ionizing radiation incident at a detector of a gamma-ray imager, and the calibration data comprises a first energy spectrum acquired when the detector is irradiated via radiation from a radioisotope in a scintillator crystal of the gamma-ray imager and a second energy spectrum corresponding to an isotope that is external to the scintillator crystal, and
determining an energy calibration in which first and second energy signals corresponding to first and second spectral features from the first energy spectrum are applied to a nonlinear energy correction to generate first and second calibrated energy signals corresponding to first and second calibrated spectral features having different distances on an energy scale between the first and second calibrated spectral features as compared to the first and second spectral features, the energy calibration being performed by adjusting parameters of the nonlinear energy correction to optimize agreement between (1) locations, on the energy scale, of first and second reference spectral features of a reference spectrum that represents absorbed radiation energy with respect to the first energy spectrum, (2) locations, on the energy scale, of the first and second calibrated spectral features, and (3) a location on the energy scale of a third reference spectral feature with respect to the second energy spectrum and a location of a third calibrated spectral feature.

27. The method according to claim 26, wherein at least one of the first, second, or third reference spectral feature is an emission peak at an energy selected from the group consisting of: 59.5, 81, 122, 202, 307, 356, 511 and 662 keV.

* * * * *